United States Patent [19]

DelMar et al.

[11] Patent Number: 4,740,637
[45] Date of Patent: Apr. 26, 1988

[54] PROCESS FOR HYDROXYMETHYLATION

[75] Inventors: Eric G. DelMar, Hopewell; Charles T. Kwiatkowski, Plainsboro, both of N.J.

[73] Assignee: FMC Corporation, Philadelphia, Pa.

[21] Appl. No.: 936,991

[22] Filed: Dec. 2, 1986

Related U.S. Application Data

[63] Continuation of Ser. No. 797,758, Nov. 12, 1985, abandoned, which is a continuation-in-part of Ser. No. 634,912, Jul. 26, 1984, abandoned.

[51] Int. Cl.$^4$ .................. C07C 29/00; C07L 29/38
[52] U.S. Cl. .................................................. 568/807
[58] Field of Search ..................... 568/807, 808, 809

[56] References Cited

U.S. PATENT DOCUMENTS

| | | | |
|---|---|---|---|
| 2,768,994 | 10/1956 | MacDonald | 260/67 |
| 2,828,286 | 3/1958 | MacDonald | 568/602 |
| 2,841,470 | 7/1958 | Berry . | |
| 2,841,570 | 7/1958 | MacDonald | 260/67 |
| 2,844,561 | 7/1958 | Bechtold et al. | 568/602 |
| 2,848,437 | 8/1958 | Langsdorf et al. | 568/602 |
| 2,848,500 | 8/1958 | Funck | 260/606 |
| 2,873,297 | 2/1959 | Ramsden | 568/809 |
| 2,957,036 | 10/1969 | Markus | 568/809 |
| 2,964,500 | 12/1960 | Jenkins | 568/602 |
| 4,024,163 | 5/1978 | Elliot et al. | 560/124 |
| 4,087,468 | 5/1978 | Solomon | 568/809 |
| 4,089,908 | 5/1978 | Kathawala | 568/807 |
| 4,130,657 | 12/1978 | Plummer | 424/305 |
| 4,214,004 | 7/1980 | Plummer | 424/305 |
| 4,329,518 | 5/1982 | Plummer | 568/807 |
| 4,402,973 | 9/1983 | Plummer | 568/807 |

OTHER PUBLICATIONS

Kirth–Othmer "Encyclopedia of Chemical Tech", vol. 11, p. 247, (1978).
Schaap et al., "Recueil", vol. 84, (1965), pp. 1200–1203.
H. Gilman and W. E. Catlin, "Cyclohexylcarbinol", *Organic Syntheses*, Coll., vol. 1, 188, (1941).
L. F. Fieser and M. Fieser, *Reagents for Organic Synthesis;* Wiley: New York, 1967; pp. 415–424.
J. Frederic Walker, *Formaldehyde*, 3rd ed; American Chemical Society, Monograph Series; Reinhold: New York, 1964; Chapter 7.
Kirk–Othmer, *Encyclopedia of Chemical Technology*, 3rd ed; Wiley: New York, 1978; vol. 1, pp. 112–123.
*Paraformaldehyde,* Product Bulletin; Celenese Chemical Company, Dallas, Tex.
*Delrin ® Acetal Resin,* Product Bulletin; DuPont, Wilmington, Del.

*Primary Examiner*—Werren B. Lone
*Attorney, Agent, or Firm*—Robert M. Kennedy; H. Robinson Ertelt; William Schmonsees

[57] ABSTRACT

Disclosed and examplified is a general method for producing methylol compounds by the reaction of an organometallic compound with formaldehyde in which the formaldehyde is generated in situ from and by the use of a high molecular weight linear formaldehyde homopolymer.

6 Claims, No Drawings

PROCESS FOR HYDROXYMETHYLATION

This application is continuation, of application Ser. No. 797,758, filed 11/12/85, which is a continuation-in-part, of application Ser. No. 634,912, filed July 26, 1984, both abandoned.

This invention is in the field of chemical processes and relates to a method for hydroxymethylating organic substrates to produce hydroxymethyl derivatives thereof, sometimes referred to herein as "methylol" compounds or "carbinols". In particular, the present invention pertains to a process for producing methylol compounds by the reaction of an organometallic compound with formaldehyde produced in situ from a high molecular weight linear formaldehyde homopolymer.

Methylol compounds of various structures abound in the chemical literature. Many such compounds are useful end-products in themselves, while others are useful as intermediates in the preparation of various useful end-products. For example, certain substituted-phenyl-methyl alcohols, such as the various biphenylmethanols disclosed in U.S. Pat. Nos. 4,130,657; 4,214,004; 4,329,518; and 4,402,973 are useful intermediates for insecticidal pyrethroid esters.

A number of methods for producing methylol compounds are available to the chemical practitioner. For compounds having one or more active carbon-bonded protons, capable of being removed by a base, and for halogen-containing compounds from which Grignard reagents can be produced, the usual method for introducing a hydroxymethyl group into the molecule, in place of the active hydrogen or the halogen, is by reaction of the Grignard reagent or a metal salt of the organic substrate with formaldehyde. This general method is illustrated in the following chemical equation in which R is an organic radical such as a hydrocarbyl radical and M is a metal or metal-halide:

$$R-M + CH_2O \rightarrow RCH_2OH.$$

Where the carbon-bonded active proton of the organic substrate is highly acidic, for example, the $\alpha$ protons of diethyl malonate, the hydroxymethylation reaction may be conducted simply and conveniently in water in the presence of a base such as potassium bicarbonate, the formaldehyde reactant being commercially available as an aqueous solution.

However, for Grignard or similar hydroxymethylation reactions where the organometallic substrate is subject to decomposition by water, generally where the $pK_b$ value for the organometallic material is lower than about $-5$, the use of aqueous formaldehyde is contraindicated. In such cases precautions must be taken to exclude water from the reaction mixture to preserve the integrity of the organometallic substrate for reaction with the formaldehyde. Generally, the formaldehyde reactant is generated from the solid polymer paraformaldehyde which depolymerizes or "unzips" to produce formaldehyde vapors. The depolymerization is facilitated by heat and is usually accomplished either in situ on heating the reaction mixture containing the paraformaldehyde or by pyrolyzing the paraformaldehyde in a separate vessel and conducting the vapors so produced into the hydroxymethylation reaction vessel.

The use of paraformaldehyde directly as a source of dry formaldehyde, however, has not been entirely satisfactory inasmuch as paraformaldehyde itself is not anhydrous, but contains a certain amount of free water in addition to the chemically combined water that is part of the paraformaldehyde molecule itself and is released in the unzipping process. The Kirk-Othmer Encyclopedia of Chemical Technology, 3rd ed; John Wiley & Sons, New York, 1978; Vol. 11; page 247 states that commercial paraformaldehyde (average molecular weight of about 600) in powder form contains up to 5% free and combined water and in flake form, up to 9%. Thus, use of commercial paraformaldehyde as such in a Grignard or similar organometallic hydroxymethylation reaction as a source of the requisite formaldehyde may result in the inclusion in the reaction mixture of up to 5% or more of water and the destruction of an equivalent amount of the organometallic reagent.

While formaldehyde vapors may be generated by the pyrolysis of paraformaldehyde outside the hydroxymethylation reaction vessel and subjected to appropriate drying conditions prior to bringing it into contact with the organometallic substrate, such a method adds an additional step to the hydroxymethylation process and may unduly subject the worker and other nearby personnel to the possibility of coming into contact with formaldehyde vapor or dust which is highly irritating, particularly to the eyes and respiratory tract, and may cause skin sensitization or dermatitis.

The present invention represents an improvement over the prior art method of hydroxymethylation in that an inherently drier source of formaldehyde than previously used is employed in the present process thereby reducing aqueous decomposition of the organometallic substrate and allowihg for increased yields of the desired carbinol products. Furthermore, the present high molecular weight linear formaldehyde homopolymer, like paraformaldehyde, may be added directly to the reaction mixture allowing the formaldehyde being formed to be consumed in the desired reaction concomitantly with its formation, thereby reducing the risk to personnel of exposure to formaldehyde fumes.

In the present invention, the requisite formaldehyde is generated in situ from and by the use of a high molecular weight linear formaldehyde homopolymer. The high molecular weight formaldehyde homopolymers useful in the present invention are polyoxymethylene compounds having a molecular weight of at least about 10,000. The polymers are composed of repeating oxymethylene units which form a linear acetal chain $\sim O-CH_2-O-CH_2\sim$ and are terminated at each end by a hydroxy group or by a labile end-capping group such as an ester group, or are terminated at one end by a non-labile end-capping group such as an ether group and at the other end by a labile end-capping group. Polymers that are capped at only one end, by a labile or a non-labile end-capping group, are also useful in the present process and are within the scope of the present invention. Labile end-capping groups are groups that are removable under the conditions of the hydroxymethylation process, whereas non-labile groups are not removable under such conditions. In order for a formaldehyde homopolymer of appropriate molecular weight to be capable of being depolymerized or unzipped to produce formaldehyde under typical hydroxymethylation process conditions and, therefore, to be suitable for use in the present process, it is necessary that at least one terminal of the formaldehyde polymer be occupied by a hydroxy group or a labile end-capping group.

It is well known in the art of polymer chemistry, as disclosed in U.S. Pat. No. 2,964,500, that polymer compositions, by virtue of limitations inherent in the methods known and used in the art for producing them, are not homogeneous but are mixtures of molecules of various molecular weights generally concentrated within a narrow range. Polymer compositions are also inexact with respect to end-caps. For example, in a composition of polymers having an ether group or an ester group at one end and a hydroxy group at the other, a small portion of the composition will likely consist of polymers capped at both ends as well as completely uncapped polymers. Therefore, it will be understood that molecular weights recited herein for formaldehyde polymers useful in the present process are average molecular weights and that some small portion of the polymer composition may differ from the major portion of the composition. The limitations described herein to define the formaldehyde polymers suitable for use in the present process are fully met if met by the polymers which constitute the major portion of a polymer composition.

The formaldehyde homopolymers useful herein may have an average molecular weight up to about 1,000,000 or higher. The average molecular weight will usually be in the range of 10,000 to 200,000, preferably in the range of 15,000 to 150,000, and more preferable in the range of 20,000 to 100,000. Those materials having an average molecular weight in the range of about 25,000 to 75,000 are especially preferred. Included among this last group of preferred polymers are polyoxymethylene diacetates such as the Delrin brand of acetal homopolymer resins sold by E.I. du Pont de Nemours & Co., Inc., Wilmington, Delaware. Polyoxymethylene diacetates having an average molecular weight of about 50,000, such as Delrin 500, are particularly desirable. Suitable formaldehyde polymers are also described in various patents and literature in the art. Both the polyoxymethylene glycol starting materials and diacetate products described in U.S. Pat. No. 2,964,500, as well as the polyoxymethylene products described in U.S. Pat. Nos. 2,768,994; 2,828,286; 2,841,570; and 2,848,437, all of which patents are incorporated herein by reference, are suitable for use in the present process. The polyoxymethylene products disclosed in U.S. Pat. No. 2,844,561, incorporated herein by reference, and which have incorporated in their structures a small amount of an amine polymerization initiator are also generally useful in the present invention but are not preferred. Other references disclosing the preparation and properties of high molecular weight formaldehyde homopolymers, including materials useful herein, are "The Kirk-Othmer Encyclopedia of Chemical Technology", 3rd ed.; John Wiley & Sons, New York; 1978; Vol. 1; pages 112–123 and "Formaldehyde"; ACS Monograph Series; J. Frederic Walker, Ed.; 3rd ed; Reinhold Publishing Corp., New York; 1964; Chapter 7, especially pages 179–191, both of which are also incorporated herein by reference.

The high molecular weight linear formaldehyde polymers useful in the present invention are compounds of the formula

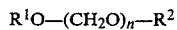

$$R^1O-(CH_2O)_n-R^2 \qquad I$$

wherein $R^1$ and $R^2$ are independently hydrogen or an end-cap group that is removable under the conditions employed in the hydroxymethylation process. One of $R^1$ and $R^2$, but not both, may also be a group that is not removable under the hydroxymethylation conditions. Thus, either uncapped or certain end-capped polymers may be used.

Uncapped formaldehyde polymers and polymers capped at only one terminal may unzip on standing to release formaldehyde. As with paraformaldehyde, depolymerization of the higher molecular weight uncapped or partially capped polymers useful herein is facilitated by heat.

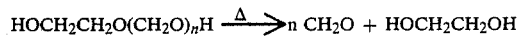

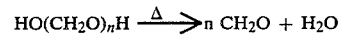

Formaldehyde polymers end-capped at both terminals offer an advantage over the corresponding uncapped materials in that they are storage-stable and will not unzip to release formaldehyde fumes until removal of at least one of the end-caps.

End-caps that are not removable under hydroxymethylation process conditions, and which may be present at one terminal but not both, include typical ether forming groups such as alkyl, aryl, and arylalkyl radicals and substituted derivatives thereof, for example, methyl, methoxyethyl, hydroxyethyl, hydroxypolyethoxyethyl, methoxypolyethoxyethyl, polyethoxyethyl, phenyl, and benzyl.

End-caps that are removable under hydroxymethylation process conditions include acyl and similar ester forming groups that are reactive themselves toward the organometallic substrate and are ultimately eliminated from the polymer leaving the previously capped end of the molecule uncapped and free to depolymerize. Typical such removable end-caps are radicals such as —C-Q—$R^3$ or —P(Q)$R^4R^5$ wherein $R^3$, $R^4$ and $R^5$ independently are optionally substituted alkyl, alkoxy, alkylthio, aryl, aryloxy, arylthio, arylalkyl, arylalkoxy, or arylalkylthio and Q is O or S. Preferably, $R^3$, $R^4$, and $R^5$ are independently selected from alkyl, aryl, and arylalkyl each of which may be substituted. A preferred end-cap ($R^1$ or $R^2$ or both) is the radical —CO—$R^3$, especially —CO—CH$_3$. In a preferred embodiment of the invention, the formaldehyde polymer is a polyoxymethylene diacetate ($R^1=R^2=$—CO—CH$_3$) having an average molecular weight in the range of about 25,000 to 75,000, particularly the material having an average molecular weight of about 50,000. Use of the corresponding glycol ($R^1=R^2=$hydrogen) also represents a preferred embodiment of the invention. It is known in the art that certain types of organometallic compounds such as organozinc halides are unreactive towards esters. Where such an organometallic reactant is to be used in the present process, it will, of course, be necessary to select a formaldehyde polymer in which at least one of $R^1$ and $R^2$ is hydrogen. Examples of removable end-caps are radicals such as

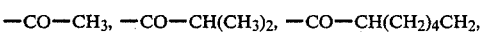

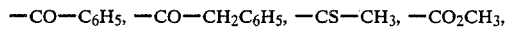

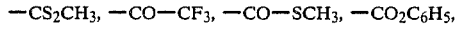

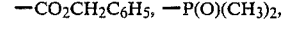

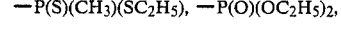

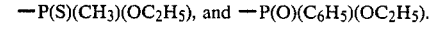

Any alkyl or aryl substituent or portion of a substituent herein may be substituted, for example, with halogen such as fluorine, chlorine, or bromine, cyano, nitro, hydroxy, alkoxy, alkylthio, or the like. Additionally, any aryl group may be substituted with alkyl. Any alkyl may be a straight chain, branched chain, or cyclic radical, frequently a lower alkyl of 1 to 8 (preferably 1 to 4) carbon atoms. Any aryl group herein may be a hydrocarbyl radical such as phenyl or a heteroaryl radical, for example, furyl, thienyl, pyridyl, pyrimidyl, oxazolyl, pyrrolyl, isoxazolyl, thiazolyl, or isothiazolyl. Halogenated alkyl or aryl groups may have one or more same or different halogen atoms.

The high molecular weight formaldehyde polymers described above are useful as a source of formaldehyde reactant in hydroxymethylation processes in which an organometallic substrate is reacted with formaldehyde to produce a methylol compound. Since the present polymers represent a source of substantially anhydrous formaldehyde, they are especially useful in those instances where the organometallic substrate is sensitive to water.

The present high molecular weight formaldehyde polymers are pulverulent solids and are advantageously employed in the present process in the form of a fine powder. It is preferred, for increased reaction rates, that the particle size be sufficiently small for the powder to pass through a 50 mesh U.S. sieve. It is desirable, therefore, to pulverize or grind coarser grade material to obtain a fine particle size.

The organometallic compound is any compound such as phenylmagnesium chloride or phenyllithium which reacts with formaldehyde under anhydrous hydroxymethylation conditions to produce a carbinol. For example, the organometallic compound may be an organomagnesium halide compound or an organozinc halide compound in which the halide is a chlorine, bromine, or iodine atom, an organolithium compound, an organosodium compound, an organopotassium compound, or the like. Frequently, the organometallic compound will be an organomagnesium halide compound. The organic moiety will generally be strongly associated with the metal moiety via an ionic carbon-to-metal bond, although the degree of association will generally vary with the polarity of the solvent used in the hydroxymethylation process. The organic moiety may be aromatic or non-aromatic, it may be a hydrocarbyl radical or contain one or more heteroatoms, and it may or may not have one or more points of unsaturation as, for example, an alkynyl radical R—C≡C—.

For example, the organic moiety may be a substituted or unsubstituted alkyl, alkenyl, alkynyl, or aryl radical, including heterocyclic and hetero-substituted radicals.

Thus, a variety of structural types of organometallic compounds are useful herein, including structural types represented by

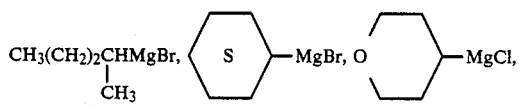

$C_6H_5CH_2MgCl$,     4-$(CH_3S)C_6H_4MgCl$,
$CH_3(CH_2)_5CH=CHMgCl$,     $CH_2=CHCH_2MgCl$,
$CH_3(CH_2)_3C\equiv CLi$,     $CH_3(CH_2)_3CH=CH-C\equiv CLi$,
$C_6H_5Li$,     4—$(Cl)C_6H_4MgBr$,     2—$(CH_3)C_6H_4MgCl$,
2—$(CH_3)$—3—$(Cl)C_6H_3MgBr$,     2—$(CH_3)$—3—$(C_6H_5)C_6H_3MgCl$,

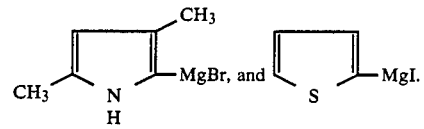

In a preferred embodiment of the present invention, the organometallic substrate is an arylmagnesium halide, for example, a substituted or unsubstituted phenylmagnesium halide. Phenylmagnesium halides of particular interest include those of the formula

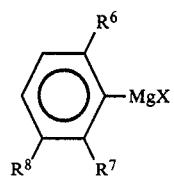

II in which X is chlorine, bromine, or iodine and $R^6$, $R^7$, and $R^8$ are independently hydrogen, halogen such as chlorine, or lower alkyl. $R^8$ may also be phenyl which may be substituted with halogen or lower alkyl. The carbinol products of this embodiment are useful intermediates for insecticidal pyrethroid esters, especially where $R^6$ is hydrogen or methyl, more especially hydrogen, $R^7$ is methyl, and $R^8$ is chlorine or, particularly phenyl.

The present process is illustrated for a preferred embodiment in the following chemical equation:

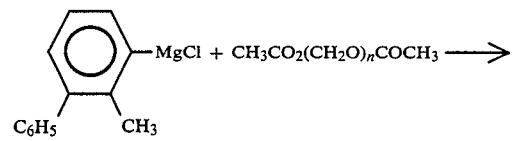

IIa     Ia

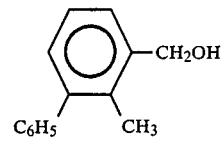

III

Reaction of the organometallic compound with the polyoxymethylene diacetate results in the removal of one or both acetyl groups from the formaldehyde polymer, and the resulting polymer product then depolymerizes to generate formaldehyde which reacts with additional organometallic compound to produce the carbinol product.

The present process may be conducted under any reaction conditions that would be acceptable in a hydroxymethylation process involving the reaction of the same organometallic compound with formaldehyde in which the formaldehyde is generated in situ from paraformaldehyde. At least a stoichiometric amount of the formaldehyde polymer, calculated on the basis of the amount of polymerized formaldehyde present, should be employed.

In general, the organometallic compound (produced in situ or separately) is brought into contact with the high molecular weight formaldehyde polymer under substantially anhydrous conditions in the presence of a substantially inert solvent under a substantially inert atmosphere. As with similar organometallic reactions, care should be taken to exclude moisture, oxygen, and carbon dioxide, which may react with the organometallic compound, by using an inert atmosphere such as nitrogen or helium.

The reaction may be conducted under standard temperature conditions for similar reactions, generally at a temperature in the range of about 25° to 150° C., advantageously at an elevated temperature such as a temperature of about 60°, preferably up to about 100° C. Frequently, the upper temperature limit will be the boiling point of the solvent or a temperature just below the melting point of the formaldehyde polymer. Preferably, the insoluble solid formaldehyde polymer is maintained as a fine powder in the reaction mixture to facilitate the generation of formaldehyde. If allowed to melt, the polymer may agglomerate into a gummy mass which may hinder the reaction.

Any of the solvents typically used in similar organometallic reactions, such as ethers or hydrocarbon solvents, may be suitably used in the present process. Some organometallic compounds, particularly organosodium compounds, are known in the art to be highly reactive toward diethyl ether, and in such cases, as in the prior art processes, a different solvent should be selected. Tetrahydrofuran is a preferred solvent.

As in the prior art hydroxymethylation processes involving the reaction of an organometallic compound with formaldehyde and conducted under anhydrous conditions, the carbinols are produced in the present process in the form of complex salts from which the desired carbinols are freed by acid hydrolysis. This involves simply contacting the salt with water and adjusting the pH by the addition of sufficient acid or acidic material to free the carbinol from the salt. Generally, the reaction mixture is poured over ice and the mixture is made acidic by the addition of an acid such as hydrochloric acid, usually concentrated hydrochloric acid. Where the desired carbinol product is sensitive to strong acids, the hydrolysis will usually be carried out by the addition of an acidic material such as ammonium chloride, generally as a saturated aqueous solution.

The present invention is further illustrated in the following example.

EXAMPLE

SYNTHESIS OF (2-METHYL[1,1'-BIPHENYL]-3-YL)METHANOL

A. Preparation of (2-methyl[1,1'-biphenyl]-3-yl)magnesium chloride

Under a nitrogen atmosphere, 101.3 g (0.50 mole) of 3-chloro-2-methylbiphenyl (92% purity) in 75 g of dry tetrahydrofuran was added dropwise over two hours with stirring to a gently refluxing mixture of 13.1 g (0.54 mole) of fresh magnesium turnings, the heel from a previous run containing 0.21 mole of unreacted magnesium, and 75 g of dry tetrahydrofuran in a dry reaction vessel. Upon complete addition, the reaction mixture was heated at reflux for five additional hours. Gas chromatographic analysis of a quenched sample of the reaction mixture showed 1.2% of unreacted 3-chloro-2-methylbiphenyl and 92.4% of 2-methylbiphenyl. The reaction mixture was allowed to cool overnight.

B. Preparation of (2-methyl[1,1'-biphenyl]-3-yl)methanol

Under a nitrogen atmosphere, the reaction mixture from above was decanted into a clean, dry flask, leaving the unreacted magnesium turnings in the first flask. This solution, which contains (2-methyl[1,1'-biphenyl]-3-yl)magnesium chloride, was heated to reflux, and 16.5 g (0.55 mole based on formaldehyde) of polyoxymethylene diacetate (avg. mol. wgt. approx. 50,000, available commercially from E.I. du Pont de Nemours & Co., Inc., Wilmington, Delaware under the trade name Delrin 500 acetal homopolymer resin), milled to about 80 mesh, was added with stirring over three hours. Refluxing was continued for four additional hours after which the reaction mixture was allowed to cool and stand overnight. The mixture was then heated to 53° C. and was poured into a mixture of 100 g of ice, 52 g of concentrated hydrochloric acid, and 200 g of a mixture containing 95% n-octane and 5% toluene (wt/wt). This mixture was filtered and the organic phase separated. The organic solvents were distilled off, boiling range 65°–93° C. During a four hour period the solution was cooled with stirring to approximately 5° C. and was then filtered. The filter cake was washed with 100 mL of cold n-octane and air-dried for 0.5 hour. The filter cake was broken up and dried under a vacuum at 55° C. for four hours, yielding 78.9 g of (2-methyl[1,1'-biphenyl]-3-yl)methanol (89.9% purity), a yield of 70.8% of theory.

We claim:

1. A method for producing the compound of the formula

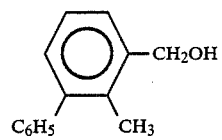

I which comprises (a) treating the compound of the formula

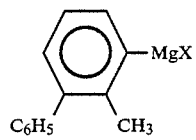

II in which X is a chlorine, bromine, or iodine atom, with a formaldehyde polymer of the formula

$R^1O-(CH_2O)_n-R^2$ having an average molecular weight in the range of about 20,000 to 100,000 and in which $R_1$ and $R^2$ are independently hydrogen, a non-labile radical selected from the group consisting of alkyl, aryl, arylalkyl, and substituted derivatives thereof, or a labile radical of the formula $-CQ-R^3$ or $-P(Q)R^4R^5$ in which $R^3$, $R^4$, and $R^5$ are independently selected from alkyl, alkoxy, alkylthio, aryl, aryloxy, arylthio, arylalkyl, arylalkoxy, arylalkylthio, and substituted derivatives thereof and Q is oxygen or sulfur, with the proviso that at least one of $R^1$ and $R^2$ is hydrogen, $-CQ-R^3$, or $-P(Q)R^4R^5$, under substantially anhydrous conditions, in the presence of a substantially inert atmosphere, at a temperature in the range of about 25° C. to a temperature below the melting point of the formaldehyde polymer, to form a salt of the compound of formula I, and (b) treating the salt of the compound of formula I with an acid or an acidic material in the presence of water to produce the compound of formula I.

2. The method of claim 1 in which $R^1$ and $R^2$ are independently selected from hydrogen and —CO—$R^3$ in which $R^3$ is lower alkyl.

3. A method for producing the compound of the formula

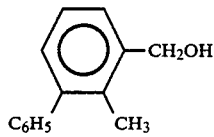

I which comprises (a) treating the compound of the formula

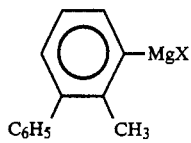

II in which X is a chlorine, bromine, or iodine atom, with a polyoxymethylene diacetate of the formula $$CH_3CO_2(CH_2O)_nCOCH_3$$

having an average molecular weight in the range of about 20,000 to 100,000, under substantially anhydrous conditions, in the presence of a substantially inert atmosphere, at a temperature in the range of about 25° C. to a temperature below the melting point of the polyoxymethylene diacetate, to form a salt of the compound of formula I, and (b) treating the salt of the compound of formula I with an acid or an acidic material in the presence of water to produce the compound of formula I.

4. The method of claim 3 in which the polyoxymethylene diacetate has an average molecular weight of about 50,000.

5. In a hydroxymethylation process for producing a methylol compound, which comprises reacting an organometallic compound with formaldehyde under substantailly anhydrous conditions in the presence of a substantially inert solvent and under a substantially inert atmosphere to give a salt of the methylol compound and treating the salt of the methylol compound with an acid or an acidic material in the presence of water to produce the methylol compound, the improvement therein which comprises:

generating the formaldehyde in situ from and by the use of a polyoxymethylene diacetate of the formula having an average molecular weight of about 50,000.

6. The process of claim 5 in which the organometallic compound is an organolithium compound or an organomagnesium halide compound.

* * * * *

UNITED STATES PATENT AND TRADEMARK OFFICE
CERTIFICATE OF CORRECTION

PATENT NO. : 4,740,637
DATED : April 26, 1988
INVENTOR(S) : Eric G. DelMar and Charles T. Kwiatkowski It is certified that error appears in the above-identified patent and that said Letters Patent is hereby corrected as shown below:

Column 10, line 29, "having an" should read --$CH_3CO_2(CH_2O)_nCOCH_3$ having an--.

Signed and Sealed this

Fourth Day of August, 1992

Attest:

DOUGLAS B. COMER

*Attesting Officer*  Acting Commissioner of Patents and Trademarks